United States Patent
Hunter et al.

(10) Patent No.: US 9,884,269 B2
(45) Date of Patent: Feb. 6, 2018

(54) METHODS AND SYSTEMS FOR SELECTIVE HYDROGEN GAS EXTRACTION FOR DISSOLVED GAS ANALYSIS APPLICATIONS

(71) Applicant: General Electric Company, Schenectaday, NY (US)

(72) Inventors: James Christopher Hunter, Lisburn (GB); Grainne Black, Lisburn (GB)

(73) Assignee: General Electric Company, Schenectady, NY (US)

( * ) Notice: Subject to any disclaimer, the term of this patent is extended or adjusted under 35 U.S.C. 154(b) by 64 days.

(21) Appl. No.: 14/965,450

(22) Filed: Dec. 10, 2015

(65) Prior Publication Data

US 2017/0165592 A1 Jun. 15, 2017

(51) Int. Cl.
   *B01D 19/00* (2006.01)
   *B01D 53/22* (2006.01)
   (Continued)

(52) U.S. Cl.
   CPC ......... *B01D 19/0031* (2013.01); *B01D 71/64* (2013.01); *C01B 3/0015* (2013.01); *G01N 33/005* (2013.01); *G01N 33/2841* (2013.01)

(58) Field of Classification Search
   CPC .. B01D 19/0031; B01D 53/228; B01D 71/64; B01D 2256/16; G01N 33/2841; G01N 2001/4016
   See application file for complete search history.

(56) References Cited

U.S. PATENT DOCUMENTS 3,866,460 A * 2/1975 Pearce, Jr. ............... G01N 7/10
                                                361/35
4,058,373 A * 11/1977 Kurz ................. G01N 33/2841
                                                73/19.1

(Continued)

OTHER PUBLICATIONS

Tsukioka, H. et al., "Apparatus for Continuously Monitoring Hydrogen Gas Dissolved in Transformer Oil", IEEE Transactions on Electrical Insulation, vol. EI-16, No. 6, Dec. 1981, pp. 502-509.*

*Primary Examiner* — Jason M Greene
(74) *Attorney, Agent, or Firm* — Eversheds Sutherland (US) LLP

(57) ABSTRACT

Systems and methods for selectively extracting hydrogen gas dissolved in oil are provided. In one embodiment, a system includes a selectively permeable membrane provided at a point of contact between oil and a sensor chamber. The selectively permeable membrane has a hydrogen specificity and a thickness selected to minimize detection of further gasses dissolved in the oil by a hydrogen gas sensor cross-sensitive to the further gasses. The selectively permeable membrane can include polyimide. The further gasses include carbon monoxide, acetylene, and ethylene. The system can include a further membrane and a porous metal disc. The porous metal disc is bound to the selectively permeable membrane by using the further membrane as an adhesive layer and by applying pressure and temperature. The porous metal disc supports the selectively permeable membrane and the further membrane against pressure of the oil when exposed to a vacuum. The further membrane includes fluorohydrocarbons.

20 Claims, 4 Drawing Sheets

(51) Int. Cl.
    *B01D 71/64*     (2006.01)
    *G01N 33/28*     (2006.01)
    *C01B 3/00*     (2006.01)
    *G01N 33/00*     (2006.01)

(56) References Cited

U.S. PATENT DOCUMENTS

| | | | | |
|---|---|---|---|---|
| 5,339,672 | A * | 8/1994 | Spicar | G01N 33/2841 210/188 |
| 5,749,942 | A * | 5/1998 | Mattis | B01D 19/0031 95/46 |
| 6,037,592 | A * | 3/2000 | Sunshine | G01N 33/2841 250/343 |
| 6,324,891 | B1 * | 12/2001 | Gibeault | G01N 33/2841 73/19.01 |
| 2005/0086998 | A1 * | 4/2005 | Qin | B01D 19/0031 73/31.07 |
| 2006/0032742 | A1 * | 2/2006 | Babes-Dornea | G01N 33/2841 204/400 |
| 2009/0166197 | A1 * | 7/2009 | Grincourt | G01N 27/4045 204/412 |
| 2010/0077828 | A1 * | 4/2010 | Herz | G01N 33/2841 73/1.03 |
| 2011/0175623 | A1 * | 7/2011 | Shrinet | G01N 33/2841 324/537 |
| 2014/0329328 | A1 * | 11/2014 | Mahoney | G01N 33/2841 436/60 |
| 2016/0231303 | A1 * | 8/2016 | Park | G01N 33/2841 |

* cited by examiner

300 

Select a selectively permeable membrane having a hydrogen specificity and a thickness allowing to minimize detection of further gasses dissolved in oil by a hydrogen gas sensor, the hydrogen gas sensor being cross-sensitive to the further gases and associated with the sensor chamber
302

Provide the selectively permeable membrane at a point of contact between oil and the sensor chamber
304

FIG. 3

METHODS AND SYSTEMS FOR SELECTIVE HYDROGEN GAS EXTRACTION FOR DISSOLVED GAS ANALYSIS APPLICATIONS

TECHNICAL FIELD

The disclosure relates to detecting and measuring the concentration of gases dissolved in oil, and, more particularly, to systems and methods for selective hydrogen gas extraction for a dissolved gas analysis in transformer oil.

BACKGROUND

Dissolved gas analysis (DGA) is a procedure that can be utilized to analyze gases in insulating oil. The insulating oil can be used in a transformer. The DGA can include determining a type of gas, a concentration of gas, and a rate of production of gas in the insulating oil of the transformer. The results of the DGA can be indicative of electrical faults in the transformer and may be used to predict breakdowns of the transformer.

Existing methods for studying concentration of a hydrogen gas in transformer oil usually involve taking a probe of the transformer oil. The gases dissolved in the transformer oil can be extracted and analyzed using a gas chromatographer with a hydrogen sensor. Generally, hydrogen sensors used to determine a concentration of hydrogen are known for being cross-sensitive to other gases, such as carbon monoxide, ethylene, and acetylene. Therefore, a hydrogen concentration measured by a hydrogen sensor may be affected by a concentration of, for example, carbon monoxide. Hydrogen gas sensors, for example, electrochemical sensors, are also known for poor performance in a humid environment. Additionally, the humid environment can reduce the life of a hydrogen gas sensor.

Accurate determination of a hydrogen concentration in transformer oil is important to determining the health of a transformer. If a hydrogen measurement is affected by cross-sensitivity to other gases, the accuracy of such determination will decrease.

SUMMARY OF THE DISCLOSURE

This disclosure relates to systems and methods for selective hydrogen gas extraction for a dissolved gas analysis in transformer oil. Certain embodiments can facilitate accurate measurement of a hydrogen concentration dissolved in the transformer oil.

According to one embodiment of the disclosure, a method for selectively extracting hydrogen gas dissolved in oil is provided. The method can include selecting a selectively permeable membrane having a hydrogen specificity and a thickness operable to minimize detection of further gases dissolved in the oil by a hydrogen gas sensor. A hydrogen gas sensor cross-sensitive to the further gases can be located inside a sensor chamber. The method may provide the selectively permeable membrane at a point of contact between the oil and the sensor chamber.

In certain embodiments of the disclosure, the selectively permeable membrane includes polyimide. The further gases dissolved in oil can include at least one of the following: carbon monoxide, acetylene, and ethylene. The thickness and the hydrogen specificity of the selectively permeable membrane can be further selected to result in a measurable hydrogen signal for the hydrogen gas sensor. The thickness of the selectively permeable membrane can be selected based on an area of contact of the selectively permeable membrane and oil. In certain embodiments of the disclosure, the relative cross-sensitivity of the hydrogen gas sensor to the further gases can be reduced to less than 3%.

In certain embodiments of the disclosure, the method may include applying a further membrane. The further membrane can be attached to the selectively permeable membrane and capable of binding the selectively permeable membrane to a porous metal surface. In certain embodiments of the disclosure, the further membrane includes fluorohydrocarbons.

In certain embodiments of the disclosure, the method includes binding the selectively permeable membrane to a porous metal disc by using the further membrane as an adhesive layer and applying pressure and temperature. The porous metal disc is operable to provide a support for the selectively permeable membrane and the further membrane against pressure of the oil. The porous metal disc can be laminated to protect the selectively permeable membrane and the further membrane from exposure to a vacuum.

According to another embodiment of the disclosure, a system for selectively extracting hydrogen gas dissolved in oil is provided. An example system includes a selectively permeable membrane provided at a point of contact between oil and a sensor chamber. The selectively permeable membrane has a certain hydrogen specificity and thickness. The hydrogen specificity and thickness can be selected to minimize detection of further gases dissolved in the oil by a hydrogen gas sensor. The hydrogen gas sensor can be located in the sensor chamber and be cross-sensitive to the further gases.

In certain embodiments of the disclosure, the selectively permeable membrane includes polyimide. The further gasses dissolved in oil can include at least one of the following: carbon monoxide, acetylene, and ethylene. The hydrogen specificity and thickness can be selected to obtain a measurable hydrogen signal. The thickness of the selectively permeable membrane can be selected based on an area of contact of the selectively permeable membrane and oil. In some embodiments of the disclosure, the relative cross-sensitivity of the hydrogen gas sensor to the further gasses can be reduced to less than 3%.

In certain embodiments of the disclosure, the system can include a further membrane. The further membrane can be attached to the selectively permeable membrane and capable of binding the selectively permeable membrane to a porous metal surface. In some embodiments, the further membrane includes fluorohydrocarbons.

In certain embodiments of the disclosure, the system includes a porous metal disc. The porous metal disc can be bound to the selectively permeable membrane with the further membrane as an adhesive layer and by applying pressure and temperature. The porous metal disc is operable to provide support for the selectively permeable and further membranes against the pressure of the oil. The porous metal disc can be laminated to protect the selectively permeable and further membranes from exposure to a vacuum.

Other embodiments, systems, methods, features, and aspects will become apparent from the following description taken in conjunction with the following drawings.

BRIEF DESCRIPTION OF THE DRAWINGS

FIG. 3 is a process flow diagram illustrating a method for selectively extracting hydrogen gas dissolved in oil, in accordance with certain example embodiments of the disclosure.

DETAILED DESCRIPTION

Example embodiments of the disclosure will be described more fully hereinafter with reference to the accompanying drawings, in which some, but not all, embodiments are shown. Indeed, the disclosure may be embodied in many different forms and should not be construed as limited to the embodiments set forth herein; rather, these embodiments are provided so that this disclosure will satisfy applicable legal requirements. Like numbers refer to like, but not necessarily the same or identical, elements throughout.

Certain embodiments of the disclosure concern methods and systems for selective hydrogen gas extraction for DGA in transformer oil that can facilitate measurements of the concentration of hydrogen dissolved in transformer oil.

In certain example embodiments of the disclosure, a method for selectively extracting hydrogen gas dissolved in oil includes selecting a selectively permeable membrane. The selectively permeable membrane has a hydrogen specificity and a thickness operable to minimize detection of further gases dissolved in oil by a hydrogen gas sensor. The hydrogen gas sensor that is cross-sensitive to the further gases can be located in a sensor chamber. The method may allow providing the selectively permeable membrane at a point of contact between the oil and the sensor chamber.

Technical effects of certain embodiments of the disclosure may provide a method for selectively extracting hydrogen gas from oil containing other gases, such as carbon monoxide, ethylene, acetylene, and water vapor. Embodiments of the disclosure may allow the use of hydrogen sensors that are cross-sensitive to other gases to reliably measure hydrogen concentration. Further technical effects of certain embodiments of the disclosure may allow extracting hydrogen gas from transformer oil in a passive manner without applying moving mechanical parts and devices such as pumps. The disclosed embodiments may facilitate humidity control by providing a stable environment to humidity dependent or sensitive sensors. The use of sensors that are humidity dependent and cross-sensitive to gases other than hydrogen may result in reduction of unplanned costs for the DGA in transformer oil.

The following provides the detailed description of certain example embodiments related to systems and methods for selective hydrogen gas extraction using the DGA in transformer oil.

Figure 1:
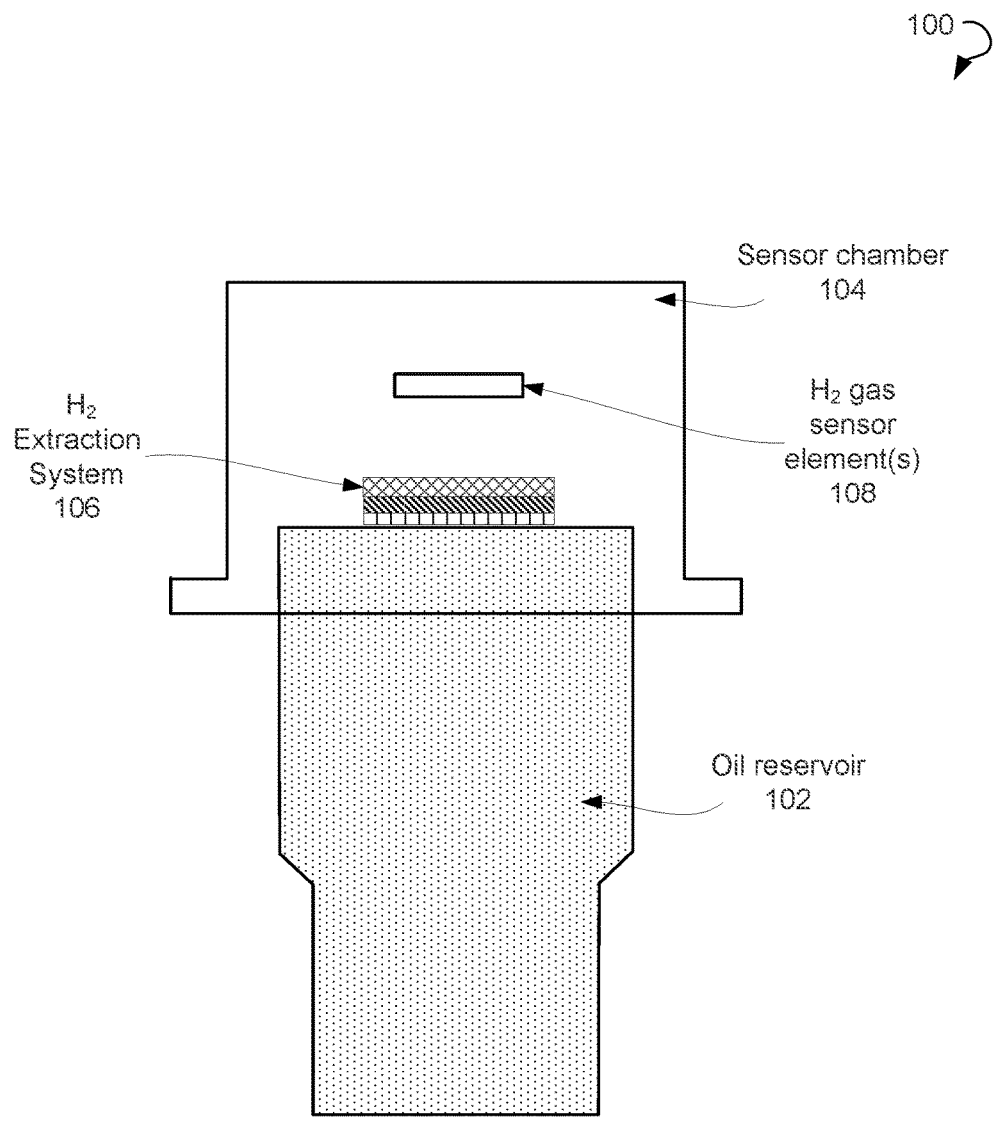
FIG. 1 is a block diagram illustrating an example environment suitable for implementing systems and methods for selective hydrogen gas extraction.

FIG. 1 is a block diagram illustrating an example environment 100 suitable for implementing systems and methods for selective hydrogen gas extraction. The environment 100 may include an oil reservoir 102, a sensor chamber 104, a hydrogen extraction system 106, and hydrogen gas sensor element(s) 108. In certain embodiments, the hydrogen extraction system 106 is placed at a gas extraction interface, i.e. at a point of contact of oil and the sensor chamber.

According to various embodiments of the disclosure, the hydrogen extraction system 106 is operable to permit substantially only hydrogen gas to permeate between the oil reservoir 102 and the sensor chamber 104. The hydrogen extraction system 106 can prevent other gases dissolved in the oil, such as carbon monoxide, ethylene and acetylene, from permeating between the oil reservoir 102 and the sensor chamber 104 and, as result, reduce or minimize the presence of the other gases in the sensor chamber 104. Thus, if a hydrogen gas sensor element(s) 108 is cross-sensitive to other gases, the hydrogen gas sensor element(s) 108 can measure substantially only the concentration of hydrogen. Therefore, no correction due to the concentration of other gases is needed. In some embodiments, the cross-sensitivity of the hydrogen gas sensor element(s) can be reduced to less than 3%. In certain embodiments, hydrogen gas sensor elements may include an electrochemical sensor.

In certain embodiments of the disclosure, the sensor chamber 104 includes a vacuum chamber or a low pressure chamber. In various embodiments of the disclosure, the permeation of hydrogen gas between the hydrogen extraction system 106 and the sensor chamber 104 corresponds to a partition coefficient of hydrogen gas dissolved in oil.

In some embodiments of the disclosure, the sensor chamber 104 includes a chamber in which humidity is controlled. For example, the humidity level inside the sensor chamber 104 can be kept below a predetermined value. In some embodiments of the disclosure, the humidity level may be stabilized at about 22%. According to certain embodiments of the disclosure, the hydrogen extraction system 106 may be operable to prevent penetration of water vapors from the oil reservoir 102 and facilitate controlling of humidity in the sensor chamber. The control of humidity in the sensor chamber 104 may provide a stable humidity environment and allow utilizing hydrogen gas sensor element(s) 108 that are humidity dependent or humidity sensitive. Providing a stable humidity environment in the sensor chamber can extend the life of the hydrogen gas sensor element(s) 108.

In various embodiments of the disclosure, the hydrogen extraction system 106 can be stabilized against the pressure of oil in the oil reservoir 102 when exposed to a vacuum to prevent damage to the hydrogen gas sensor element(s) 108.

Figure 2:
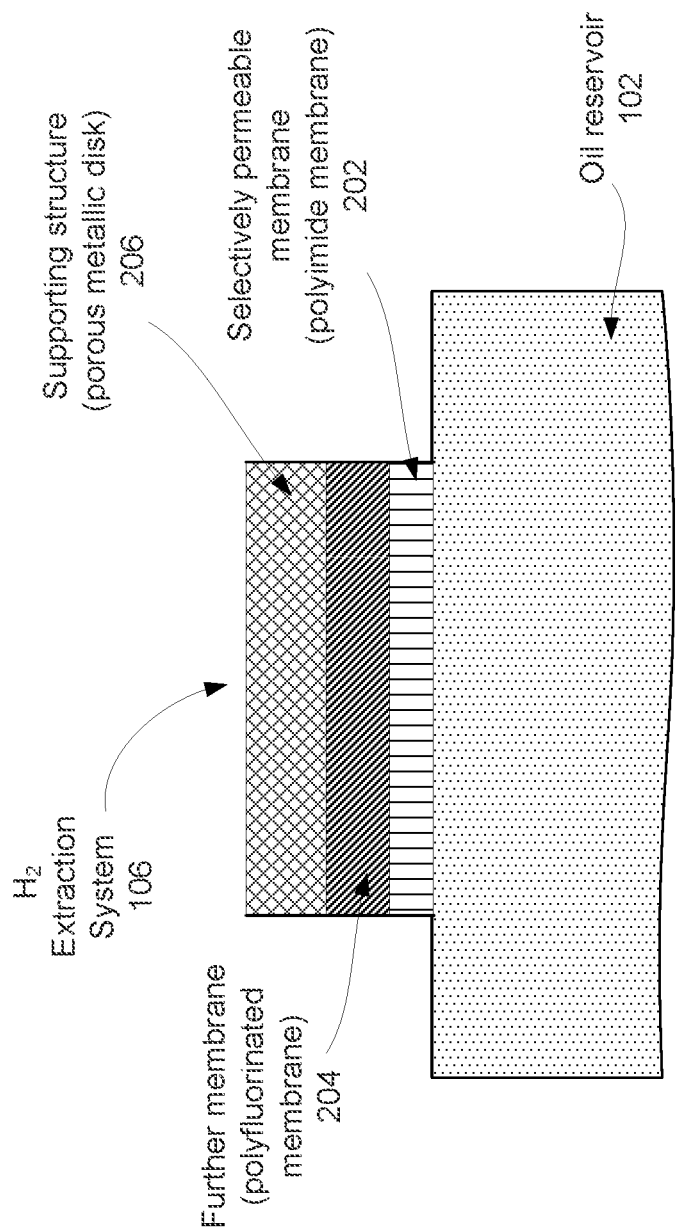
FIG. 2 is a block diagram illustrating a selective hydrogen gas extraction system, in accordance with certain example embodiments of the disclosure.

FIG. 2 shows a selective hydrogen extraction system 106, according to various examples of the disclosure. The hydrogen extraction system may include a selectively permeable membrane 202, a further membrane 204, and a supporting structure 206.

The selectively permeable membrane 202 can be placed at the area of contact with (transformer) oil in the oil reservoir 102. The hydrogen selective permeable membrane 202 can allow permeation of hydrogen gas dissolved in oil. The thickness of the selectively permeable membrane 202 and the area of contact of the polyimide membrane with the oil surface can be selected such that only hydrogen molecules permeate the hydrogen extraction system 106. At the same time, the amount of the hydrogen gas permeating the hydrogen extraction system 106 needs to be sufficient to be detected and measured by the hydrogen gas sensor element(s) 108 (as shown in FIG. 1).

In certain embodiments, the selectively permeable membrane 202 may include a polyimide membrane which allows permeation of hydrogen gas dissolved in oil while preventing other gases (such as but not limited to carbon monoxide, ethylene, and acetylene) dissolved in oil to pass through the membrane. In some embodiments of the disclosure, the selectively permeable membrane 202 can also prevent, at least partially, permeation of water vapor between the oil and oil reservoir 102.

In various embodiments of the disclosure, the further membrane 204 is operable at least to adhere the hydrogen selectively permeable membrane 202 to the supporting structure 206. The further membrane can permit passing hydrogen gas. In certain embodiments of the disclosure, the further membrane may limit (in addition to the selectively permeable membrane 202) penetration of water vapor from the oil reservoir 102 and, as a result, facilitate control of the humidity level in the sensor chamber 104 (shown in FIG. 1). In some embodiments, the further membrane includes fluorohydrocarbons. In certain embodiments of the disclosure, the further membrane includes a polyfluorinated membrane. The polyfluorinated membrane can be capable of binding a polyimide membrane to a porous metal surface.

In various embodiments of the disclosure, the supporting structure 206 is provided to ensure that the assembly of the selectively permeable membrane 202 and the further membrane 204 remains stable against oil pressure when exposed to a vacuum. At the same time, the supporting structure 206 may allow hydrogen molecules to permeate between the oil reservoir 102 and the sensor chamber 104 (shown in FIG. 1).

In some embodiments of the disclosure, the supporting structure 206 includes a porous metal disc. If the selectively permeable membrane 202 is a polyimide membrane, it can be glued to a porous metal disc using a polyfluorinated membrane as an adhesive layer and by applying heat and pressure. The porous disc can be laminated to protect the polyimide membrane and the polyfluorinated membrane from exposure to a vacuum. Without applying the polyfluorinated membrane as an adhesive layer, the polyimide membrane may not be capable of adhering to the porous metal disc.

In further embodiments of the disclosure, a supporting structure 206 can include components other than a porous metal disc (for example, a plastic mesh) for protection of the selectively permeable membrane 202 against the oil pressure when exposed to a vacuum. Therefore, components other than a polyfluorinated membrane can be used as an adhesive layer between the supporting structure 206 and the selectively permeable membrane 202.

FIG. 3 is a flow chart illustrating an example method 300 of selectively extracting hydrogen gas dissolved in oil, according to certain embodiments of the disclosure. Method 300 can be implemented in environment 100 (shown in FIG. 1) using the hydrogen extraction system 106 (shown in FIG. 2). Method 300 may commence with selecting, in operation 302, a selectively permeable membrane. The selectively permeable membrane can have a hydrogen specificity and a thickness that minimizes detection by a hydrogen gas sensor of further gases dissolved in oil. The hydrogen gas sensor can be cross-sensitive to the further gasses. The hydrogen gas sensor may be associated with a sensor chamber. In operation 304, the selectively permeable membrane is provided at a point of contact between oil and the sensor chamber.

Figure 4:
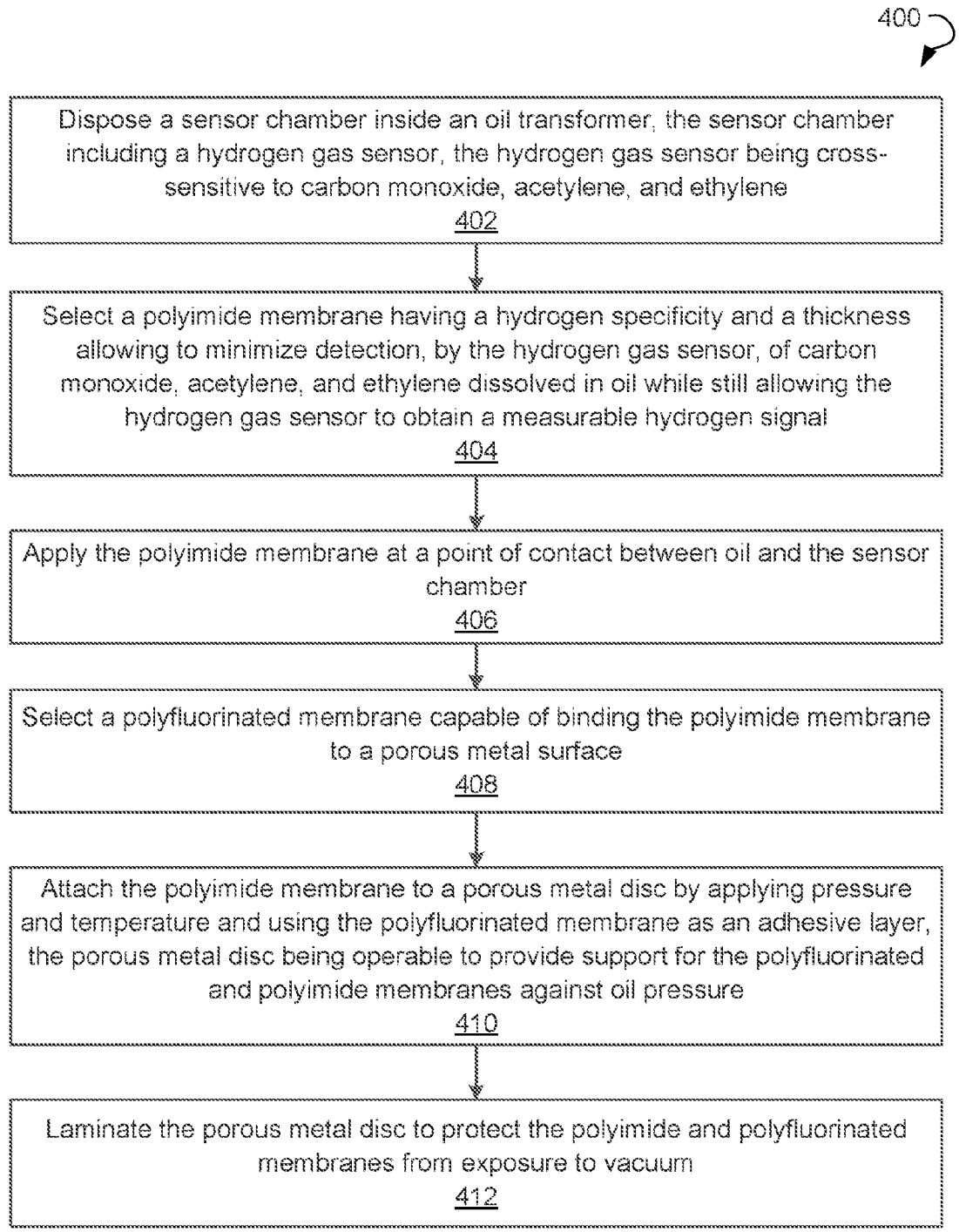
FIG. 4 is a process flow diagram illustrating a method for selectively extracting hydrogen gas dissolved in oil, in accordance with certain example embodiments of the disclosure.

FIG. 4 is a flow chart illustrating an example method 400 for selectively extracting hydrogen gas dissolved in oil, according to an embodiment of the disclosure. Method 400 can be implemented in environment 100 (FIG. 1) using a hydrogen extraction system 106 (FIG. 2). Method 400 can commence, in operation 402, with disposing a sensor chamber inside an oil transformer. The sensor chamber may include at least one hydrogen gas sensor. The hydrogen gas sensor can be cross-sensitive to at least one of the following: carbon monoxide, ethylene, and acetylene.

In operation 404, a polyimide membrane can be selected. The polyimide membrane can have hydrogen specificity and a thickness allowing minimization of detection, by the hydrogen gas sensor, of carbon monoxide, acetylene, and ethylene dissolved in oil. At the same time, the thickness of the polyimide membrane can remain sufficient to allow the hydrogen gas sensor to obtain a measurable hydrogen signal.

In operation 406, the polyimide membrane can be applied at a point of contact between oil and the sensor chamber. In certain embodiments of the disclosure, the method 400 may include selecting a polyfluorinated membrane in operation 408. The polyfluorinated membrane can be capable of binding the polyimide membrane to a porous metal surface. In operation 410, the polyimide membrane can be attached to a porous metal disc using the polyfluorinated membrane as an adhesive layer and by applying pressure and temperature. The porous metal disc can provide support for the polyimide membrane and the polyfluorinated membrane against oil pressure. The polyfluorinated membrane can be used as an adhesive layer because the polyimide membrane cannot be attached to the porous disc directly. It should be noted that using an assembly of the polyimide membrane and the polyfluorinated membrane may provide better prevention of permeation by water vapor from oil to the sensor chamber when compared to using the polyimide membrane alone.

In operation 412, the porous metal disc can be laminated to protect the polyimide membrane and the polyfluorinated membrane from exposure to a vacuum. Many modifications and other embodiments of the example descriptions set forth herein to which these descriptions pertain will come to mind having the benefit of the teachings presented in the foregoing descriptions and the associated drawings. Thus, it will be appreciated that the disclosure may be embodied in many forms and should not be limited to the example embodiments described above.

Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for selectively extracting hydrogen gas dissolved in oil, the method comprising:
   selecting a selectively permeable membrane having a hydrogen specificity and a thickness operable to minimize detection of further gases dissolved in oil by a hydrogen gas sensor, the hydrogen gas sensor being cross-sensitive to the further gases and associated with a sensor chamber;
   maintaining control of humidity proximate to the hydrogen gas sensor; and
   providing the selectively permeable membrane at a point of contact between the oil and the sensor chamber within a transformer.

2. The method of claim 1, wherein the selectively permeable membrane includes polyimide.

3. The method of claim 1, wherein the further gases include at least one of the following: carbon monoxide, acetylene, and ethylene.

4. The method of claim 1, wherein the thickness and the hydrogen specificity of the selectively permeable membrane are further selected to result in a measurable hydrogen signal for the hydrogen gas sensor.

5. The method of claim 1, wherein the thickness of the selectively permeable membrane is selected based at least in part on an area of contact of the selectively permeable membrane and oil.

6. The method of claim 1, wherein a relative cross-sensitivity of the hydrogen gas sensor to the further gases is reduced to less than 3%.

7. The method of claim 1, further comprising applying a further membrane, the further membrane being attached to the selectively permeable membrane and capable of binding the selectively permeable membrane to a porous metal surface.

8. The method of claim 7, wherein the further membrane includes fluorohydrocarbons.

9. The method of claim 7, further comprising binding the selectively permeable membrane to a porous metal disc by using the further membrane as an adhesive layer and applying pressure and temperature, the porous metal disc being operable to provide a support for the selectively permeable membrane and the further membrane against pressure of the oil.

10. The method of claim 9, further comprising laminating the porous metal disc to protect selectively permeable membrane and the further membrane from exposure to vacuum.

11. A system for selectively extracting hydrogen gas dissolved in oil, the system comprising:
a selectively permeable membrane provided at a point of contact between oil and a sensor chamber within a transformer, the selectively permeable membrane having a hydrogen specificity and a thickness selected to minimize detection of further gasses dissolved in the oil by a hydrogen gas sensor, the hydrogen gas sensor being cross-sensitive to the further gasses and associated with the sensor chamber, and the sensor chamber being humidity controlled, wherein the humidity is kept below or stabilized at a predetermined value.

12. The system of claim 11, wherein the selectively permeable membrane includes polyimide.

13. The system of claim 11, wherein the further gasses include at least one of the following: carbon monoxide, acetylene, and ethylene.

14. The system of claim 11, wherein the hydrogen specificity and the thickness are further selected to obtain a measurable hydrogen signal.

15. The system of claim 11, wherein the thickness of the selectively permeable membrane is selected based at least on an area of contact of the selectively permeable membrane and oil.

16. The system of claim 11, wherein a relative cross-sensitivity of the hydrogen gas sensor to further gasses is reduced to less than 3%.

17. The system of claim 11, further comprising a further membrane being attached to the selectively permeable membrane and capable of binding the selectively permeable membrane to a porous metal surface.

18. The system of claim 17, wherein the further membrane includes fluorohydrocarbons.

19. The system of claim 17, further comprising a porous metal disc, the porous metal disc being bound to the selectively permeable membrane by using the further membrane as an adhesive layer and by applying a pressure and a temperature, the porous metal disc being operable to provide a support for the selectively permeable membrane and the further membrane against pressure of the oil, wherein the porous metal disc is laminated to protect the selectively permeable membrane and the further membrane from exposure to vacuum.

20. A system for selectively extracting hydrogen gas in transformer oil, the system comprising:
a polyimide membrane applied at a point of contact between transformer oil and a sensor chamber within a transformer containing a hydrogen gas sensor having cross-sensitivity to carbon monoxide, acetylene, and ethylene, the polyimide membrane being operable to enable selective permeation of a hydrogen dissolved in the transformer oil into the sensor chamber and the thickness of the polyimide membrane being selected to reduce detection of carbon monoxide, acetylene, and ethylene by the hydrogen gas sensor, while the hydrogen gas sensor remains operable to obtain a measurable hydrogen signal;
a polyfluorinated membrane attached to the polyimide membrane and capable of binding the polyimide membrane to porous metal surface; and
a porous metal disc bound to the polyimide membrane using the polyfluorinated membrane as an adhesive layer and by applying pressure and temperature, the porous metal disc being operable to provide support for the polyimide membrane and the polyfluorinated membrane against pressure of the oil and the porous metal disc being laminated to prevent damage to the polyimide membrane due to vacuum.

* * * * *